United States Patent [19]

Matcham et al.

[11] Patent Number: 5,866,512
[45] Date of Patent: Feb. 2, 1999

[54] PLANT GROWTH INHIBITION USING THE R-ISOMER OF ESPROCARB

[75] Inventors: George W. Matcham, Bridgewater; Norman W. Thomas, Warren, both of N.J.

[73] Assignee: Celgene Corporation, Warren, N.J.

[21] Appl. No.: 994,865

[22] Filed: Dec. 19, 1997

[51] Int. Cl.[6] .......................... A01N 47/12; C07C 333/04
[52] U.S. Cl. .............................................. 504/305; 558/242
[58] Field of Search ............................. 504/305; 558/242

[56] References Cited

U.S. PATENT DOCUMENTS

| | | | |
|---|---|---|---|
| 3,742,005 | 6/1973 | Tilles | 260/455 A |
| 5,565,602 | 10/1996 | Matson et al. | 558/242 |

*Primary Examiner*—S. Mark Clardy
*Attorney, Agent, or Firm*—Woodcock Washburn Kurtz Mackiewicz & Norris LLP

[57] ABSTRACT

Compositions for controlling growth of plant species, and methods for using the compositions, are disclosed. The compositions contain a single-isomer enantiomeric S-benzyl thiocarbamate and are particularly useful in controlling annual weeds associated with rice, soybeans and corn.

10 Claims, No Drawings

PLANT GROWTH INHIBITION USING THE R-ISOMER OF ESPROCARB

FIELD OF THE INVENTION

The present invention is directed to stereochemically enriched thiocarbamate compositions for regulating plant growth and to methods for using the compositions.

BACKGROUND OF THE INVENTION

Weeds and other vegetation inhibit the growth of crops and other desired plants by consuming nutrients and living space which are vital to the growth of the desired plants. Attempts to solve this problem have led to the development of a wide variety of compounds which are effective as herbicides.

Thiocarbamates (alternately referred to in the chemical literature as "thiolcarbamates", the names being used interchangeably) are an important class of compounds known to be effective herbicides. In particular, S-benzyl thiocarbamates are known for control of weeds, including those weeds associated with rice crops. A number of thiocarbamates, and methods for their preparation, are described in U.S. Pat. No. 5,565,602, the disclosure of which is hereby incorporated herein by reference in its entirety. The use of S-benzyl thiocarbamates, such as S-benzyl N,N-ethyliso-butylthiocarbamate, for the control of weeds associated with rice crops is described in U.S. Pat. No. 3,742,005.

Certain thiocarbamates contain a nitrogen atom attached to a chiral carbon atom. These thiocarbamates exist as S- and R- enantiomers. One such carbamate is S-benzyl 1,2-dimethylpropyl (ethyl)thiocarbamate, available commercially as "esprocarb". Prior art disclosures of thiocarbamate compounds useful as herbicides do not discuss the separate enantiomers or suggest any potential benefits of using a single enantiomer of any of esprocarb to control plant growth.

Those skilled in the art will recognize that no single herbicide is the preferred choice for use against all unwanted plant growth. Due in part to the significant economic effect of unwanted plant growth on crop yield, research continues in efforts to identify new herbicidal compositions and methods for preparing the compositions. In particular, there is a need for herbicidal compositions showing improved effectiveness over currently used compounds against particular plant species, thereby reducing the amount of herbicidal composition needed and the concomitant expense and environmental effects. The present invention is directed to these, as well as other important ends.

SUMMARY OF THE INVENTION

It has been surprisingly and unexpectedly discovered that the R-enantiomer of S-benzyl 1,2-dimethylpropyl-(ethyl)thiocarbamate, is more effective in inhibiting the growth of certain plant species, including important annual weeds, than is the S-enantiomer. Certain compositions of the present invention contain enantiomeric thiocarbamates which are enriched in the R-isomer. These have been found to yield surprisingly good results.

It has further been found that certain thiocarbamate compositions, containing S-benzyl 1,2-dimethylpropyl-(ethyl)thiocarbamate, enriched in the R-enantiomer, are more effective in inhibiting the growth of certain plant species than are compositions containing the racemate or the S-enantiomer. This effect is quite pronounced when the effectiveness of the R-enantiomer is compared to that of the racemate.

The present invention provides, in one aspect, S-benzyl 1,2-dimethylpropyl(ethyl)thiocarbamate, enriched in the R-isomer. This compound has the formula (I):

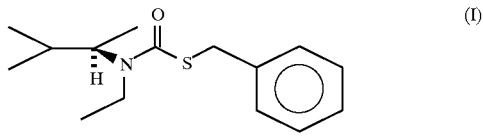

The present invention also provides methods for inhibiting growth of plants, comprising applying to the loci of the plants S-benzyl 1,2-dimethylpropyl(ethyl)thiocarbamate, enriched in the R enantiomer.

Another aspect of the present invention provides plant growth regulators comprising S-benzyl 1,2-dimethylpropyl (ethyl)thiocarbamate, enriched in the R-enantiomer, in an agriculturally acceptable carrier.

In certain preferred embodiments of the present invention, the amount of thiocarbamate present is "herbicidally effective". As used herein, the term "herbicide" means that a compound or composition negatively controls or modifies the growth of plants. Such controlling or modifying effects can include all deviations from natural development, such as killing, growth retardation, defoliation, desiccation, regulation, stunting, tillering, leaf burn, dwarfing, and the like. The term "herbicidally effective amount" is meant to include any amount of such compound or composition which causes such negative modifying effect upon the growth of plants.

The term "enriched", as used herein, means that a mixture of enantiomers contains at least about 75% of a single isomer, preferably at least about 85 percent, more preferably at least about 90 percent. In certain embodiments, a composition enriched in a single isomer can contain at least about 90 percent of that single isomer. It is generally desirable to maximize the amount of a single isomer when preparing a composition enriched in said isomer.

It will be recognized by those skilled in the art that certain herbicidal compositions are more effective in controlling the growth of plants in particular stages such as, for example pre-emergent or post-emergent stages, than are other compositions. It will further be recognized that certain herbicidal compositions are more effective in controlling plant growth at one stage than at another. Thus, it is within the purview of one skilled in the art to recognize or determine the stage and/or species for which a particular growth regulating compound is most suitable, and conversely to select an herbicidal composition for controlling the growth of a particular species.

It is generally desirable that a growth regulating composition used against undesired plant species destroy or prevent the growth of as much of an undesired plant species as feasible, such as, for example, by destroying at least about 80 to 85% of an established undesired plant. However, it will be recognized by those skilled in the art that suppression or destruction of plant growth at lower levels, particularly with some noxious and/or herbicide-resistant plants, can be commercially advantageous. Such suppression of plant growth is intended to fall within the scope of the present invention.

A quantitative measure of the herbicidal effectiveness of a compound is the "GR80". The GR80 is the amount of a compound which will provide at least 80% control of growth of an undesired plant species. In selecting an appropriate compound for controlling plant growth, the GR80 is generally considered along with environmental and economic factors. For example, it will be generally be economically preferred to use a compound which provides the lowest cost per unit area or number of plants. However, environmental considerations generally favor using the smallest quantity of a given compound that will provide acceptable results. The GR80 provides one measure of effectiveness and is useful in comparing two compounds having similar economic and/or environmental costs.

The methods and compositions of the present invention are useful in inhibiting or regulating the growth of plant species, including annual weeds. Preferably, the compounds of the present invention are differentially herbicidally active toward at least one desired plant species. By "differentially herbicidally active" is meant that the compounds may display less herbicidal activity toward a particular desired plant species as compared to their activity against one or more undesired plant species. In still more preferred embodiments, the methods and compositions of the present invention are substantially herbicidally inactive toward at least one desirable plant species. By "substantially inactive" is meant that the compound causes less than 20% damage to desired plant species. Such desirable plants are generally referred to as "crop plants". The term "crop plants", as used herein, includes any edible or non-edible, including decorative, plant species with commercial value, which is planted and cultivated for commercial use. Thus, crop plants include floral plants, trees, vegetable plants, and the like. The term "plants" is meant to include germinant seeds, emerging seedlings and established vegetation, including roots and above-ground portions.

The GR20 of an herbicidally active compound can be used to compare activity of the compound against particular desired plant species with the activity of another compound, or to compare the activity of the compound against the desired species with that against the undesired species. The GR20 is the amount of active ingredient per acre which causes 20% damage to a crop species. In selecting an herbicidal compound and the appropriate quantity of the compound for use on a particular crop species, it is generally desirable to minimize the GR80 against one or more weed species, while maximizing the GR20 for the crop species. Factors considered in reaching a balance include cost of herbicide, concentration of active ingredient in available formulations with associated storage and shipping costs, and economic value of the crop species. For example, a compound of the present invention can be considered substantially inactive toward a plant species if it has a GR20 for that species of greater than about 300 grams per acre of active ingredient (g ai/acre), preferably greater than about 400 g ai/acre, even more preferably greater than about 500 g ai/acre. However, if the GR80 of the same compound against a particular undesired species is higher than 300–500 g/acre, economic costs can be an important factor.

The amount of thiocarbamate contained in plant growth regulating compositions of the present invention can be readily determined for particular crop plants and particular weed families by persons skilled in the art. The thiocarbamate compounds can be used as the only active ingredient in a growth regulator composition, or can be used in combination with one or more other compatible agricultural chemicals, e.g., pesticides, herbicides, fungicides and/or insecticides. By "active ingredient" is meant a compound or compounds having desired activity for controlling plant growth, exclusive of any material or agent which is not active in controlling plant growth. Suitable ranges of active ingredient in plant growth regulator compositions of the present invention are from about 0.1 percent to about 50 percent, preferably from about 1 percent to about 10 percent, with more preferred ranges depending upon application, as discussed hereinbelow.

The compositions of the present invention can comprise, in addition to one or more compounds of the invention, one or more compounds not of the invention but which possess biological activity, such as plant disease control agents including fungicides, insecticides, nematicides and other pesticides. For example, it may be advantageous to apply compounds of the invention alone or in combination with other herbicides or growth regulators, also optionally mixed together with further crop protection agents such as, for example with agents for controlling phytopathogenic fungi or bacteria.

For some applications, one or more other herbicides can be added to a compound of the invention, providing additional advantages and effectiveness. Accordingly the compositions can comprise a mixture of at least one compound of formula (I) and at least one other herbicide. Preferred additional herbicides are those having complementary action in the particular application. For example, it may be desirable in some circumstances to use a compound of formula (I) in admixture with a contact herbicide. Suitable herbicides for use in combination with the compounds of the present invention include carboxylic acids and derivatives thereof, including agriculturally acceptable salts; carbamic acid derivatives, including additional thiocarbamates, phenylcarbamates, pentachlorophenol and agriculturally acceptable salts thereof; substituted ureas; diazines; benzothiadiazinones; substituted triazines; diphenyl ether derivatives; analides; cyclohexane-1,3-diones; oxyphenoxy herbicides; uracils; nitrites, and other herbicides known in the art. Suitable herbicides for use in combination with the compounds of the present invention are described in U.S. Pat. Nos.5,629,264 and 5,447,903, the disclosures of which are hereby incorporated herein by reference in their entirety. Suitable salts are generally those which readily ionize in aqueous media to form a cation or anion, and which do not have an adverse effect on the action of a herbicide, including a compound of the invention. It is also desired that the salts permit formulation of various mixtures, e.g., herbicide-antidote compositions, without undue problems of mixing, suspending, stability, application equipment use, packaging, etc.

The compositions of the present invention are effective in controlling the growth of certain annual weeds, including grasses. Furthermore, the compositions of the present invention have been shown to be more effective in the control of grass weeds in pre-emergent growth stages than in post-emergent stages.

Exemplary species the growth of which can be controlled using compositions and methods of the present invention include Setaria viridis, Echinochloa crus-galli Sorghum halepense, Digitaria sanguinalis, Agropyron repens, Cyperus esculentus, Seteria faberi, and similar species. The R-enantiomer of benzyl 1,2-dimethylpropyl (ethyl)-thiocarbamate has been found to be significantly more effective in controlling the growth of Seteria faberi, Setaria viridis Echinochloa crus-galli and Agropyron repens than is the racemic mixture or the S-enantiomer. Thus, it has now been recognized that the R-enantiomer of certain thiocarbamates is more effective than the commonly used racemic mixture in controlling the growth of some plant species. The methods and compositions of the present invention provide for increased control of the growth of certain such species as compared to currently available compositions including racemic thiocarbamates.

The compounds of the present invention can be used in controlling the growth of weeds, especially grass weeds, in association with crops and are particularly useful in controlling weeds associated with corn, rice, and soybeans. The compositions of the present invention may be advantageously employed selectively to control weeds in, for example, agronomic and horticultural crops, forestry, orchards, turf, and/or vines. The compounds of the present invention are selective or non-selective, depending on the rate applied, the combination of plants to which they are applied and whether they are applied pre- or postemergent. Such variables are understood by those skilled in the art. Generally, at higher application rates the compounds tend to be non-selective, while at lower dosage rates they tend to be selective.

The compounds of the present invention are useful both as preemergence and as postemergence herbicides, preferably as preemergence herbicides. Preemergence herbicides may be applied to the soil surface, incorporated into the soil, or sprayed onto standing water, and can be applied before, during or after seeding but before the plant to be controlled emerges. Postemergence herbicides are those which are applied after the plants have emerged, during their growth period. The compounds of the present invention may be applied to the soil surface prior to plant emergence or incorporated into the soil or other growth medium prior to planting. This incorporation can be carried out by any convenient means, including by simply mixing the compound in dry form with the soil, by applying the compound to the surface of the soil and then dishing or dragging into the soil to the desired depth, or by employing a liquid carrier.

Compositions comprising the compounds of the present invention can be applied to various loci such as the soil or the foliage. The compounds are generally taken up in a carrier or otherwise formulated so as to render them suitable for subsequent dissemination. For example, they can be formulated as wettable powders, emulsifiable concentrates, dusts, granular formulations, aerosols or flowable emulsion concentrates. In such formulations, the compounds can be extended with a liquid or solid carrier and, when desired, suitable surfactants can be employed.

The compounds of the invention can be mixed with fertilizers or fertilizing materials before application. For example, particles of a fertilizing material such as ammonium sulfate, ammonium nitrate or ammonium phosphate, can be coated with a compound of the invention. The solid compounds can be admixed in mixing or blending equipment, or can be incorporated with fertilizers in granular formulations. Any relative proportion of fertilizer can be used which is suitable for the crops and weeds to be treated. As a general guide, the herbicidal compound can be from about 3% to about 30%, preferably from about 5% to about 25% of a fertilizing composition containing the herbicidal compound and fertilizing material.

The thiocarbamate compounds of the present invention can be used in preparing compositions containing as active ingredient from about 75% to about 95% of an R-enantiomer of the formula (I). Preferably the compound is blended together with solid or liquid diluent, carrier, conditioning, wetting, dispersing and/or emulsifying and/or other surface active agents. Kaolin, bentonite, silica gel, talc, calcium carbonate, dolomite, Fuller's earth and gypsum etc. may be considered as solid diluents; various organic solvents such as aromatic hydrocarbons or ketones, preferably e.g. toluene, xylenes, trialkylbenzene mixtures, N-methyl-2-pyrrolidone, methylcyclohexanone or isophorone can be used as liquid diluents. Optionally, water can be used as a diluent or carrier. The compositions can also contain, as discussed above, other agricultural chemicals which form part of the total active ingredient content.

While this invention has been exemplified by reference to one particular thiocarbamate plant growth regulator, other members of the chemical family can also be used in connection with this invention. Thus, derivatives of the enantiomeric thiocarbamate of formula I that are substituted in the phenyl, benzylic or alkyl portions may be so employed, so long as chirality is maintained.

Compositions containing compounds of formula (I) include both dilute compositions, which are ready for immediate use, and concentrated compositions, which require dilution before use. Dilute compositions ready for use preferably contain from about 0.01% to about 2% by weight of active ingredient, while concentrated compositions can contain from about 20% to about 95% of active ingredient, although from about 20% to about 70% is usually preferred.

Solid compositions can be in the form of granules, or dusting powders wherein the active ingredient is mixed with a finely divided solid diluent. They may also be in the form of dispersible powders or grains, comprising a wetting agent to facilitate the dispersion of the powder or grains in liquid. Solid compositions in the form of a powder can be applied as foliar dusts.

Liquid compositions can comprise a solution or dispersion of active ingredient in water or an organic solvent, optionally containing a surface active agent, or can comprise a solution or dispersion of active ingredient in a water-immiscible organic solvent which is dispersed as droplets in water.

Surface active agents can be of cationic, anionic or non-ionic type. Cationic agents include quaternary ammonium compounds such as, for example, cetyltrimethylammonium bromide. Suitable anionic agents include salts and esters of sulfuric acid, such as, for example, sodium lauryl sulfate; and salts of sulfonated aromatic compounds such as, for example, sodium dodecylbenzenesulfonate, sodium, calcium and ammonium lignosulfonate. Suitable non-ionic agents include condensation products of ethylene oxide with fatty alcohols such as oleyl alcohol and cetyl alcohol, or with alkylphenols such as octyl- or nonyl phenol or octyl cresol. Other non-ionic agents include partial esters derived from long chain fatty acids, and hexitol anhydrides.

Aqueous solutions or dispersions can be prepared by dissolving the active ingredient in water or an organic solvent optionally containing one or more wetting and/or dispersing agents and, when organic solvents are used, adding the mixture so obtained to water optionally containing one or more wetting and/or dispersing agents. Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a relatively high proportion of the active ingredient, and the concentrate can then be diluted with water before use. The concentrate should withstand storage for prolonged periods of time and, after such storage, be capable of dilution with water to form aqueous preparations which remain substantially homogeneous for a sufficient time to enable them to be applied by conventional spray equipment.

A preferred form of concentrated composition comprises active ingredient which has been finely divided and dispersed in water in the presence of a surface active agent and a suspending agent. Suitable suspending agents include hydrophilic colloids such as, for example, polyvinylpyrrolidone and sodium carboxymethylcellulose, and the vegetable gums including gum acacia and gum tragacanth. Preferred suspending agents include those which impart thixotropic properties and increase the viscosity of the concentrate. Examples of preferred suspending agents include hydrated colloidal mineral silicates, such as montmorillonite, heidellite, nontronite, hectorite, saponite saucorite and bentonite. Other suitable suspending agents include cellulose derivatives and polyvinyl alcohol.

The compositions of the present invention can be applied to the locus of a plant, especially one or more undesired plants, in any amount which will give the required control of the undesired plants. The rate of application of the compounds of the invention will depend upon a number of factors including, for example, the identity of the plants whose growth is to be inhibited, the formulations selected for use and whether the compound is to be applied for foliage or root uptake. Generally a suitable rate of application of compositions of the invention for controlling plant growth is from about 0.05 to about 10 pounds of the active thiocarbamate per acre and preferably from about 0.1 to about 5 pounds per acre. Even more preferably a rate from about 0.6 to about 3 pounds per acre is used.

The thiocarbamates of the present invention can be prepared using methods well known to those skilled in the art. A general method for producing thiocarbamates is described in U.S. Pat. No. 5,565,602. Although not preferred, the single enantiomer can be obtained by separation from a racemic mixture using resolution techniques or, preferably, chiral chromatography. In the compositions of the present invention, enrichment in the R-enantiomer is desired.

Alternatively, synthesis can be carried out so that, rather than producing a racemic mixture, the process produces substantially a single enantiomer, according to methods known to those skilled in the art and exemplified herein. For example, R-transaminase can be used to prepare an amine such as R(−)-1,2-dimethylpropylamine for use as a starting material in forming R-benzyl 1,2-dimethylpropyl(ethyl) thiocarbamate. Conversely, S-transaminase is suitable in preparing the S-enantiomer. A racemic thiocarbamate mixture can be prepared using a commercially available amine such as 1,2-dimethylpropylamine.

EXAMPLES

The following examples are merely illustrative of the present invention and should not be considered limiting of the scope of the invention in any way. These examples and equivalents thereof will become more apparent to those skilled in the art in light of the present disclosure and the accompanying claims.

Example 1

Preparation of racemic S-benzyl 1,2-dimethylpropyl (ethyl)thiocarbamate a) Preparation of racemic 1,2-dimethylpropyl(ethyl)amine A mixture of bromoethane (25.0 grams (g); 229.0 millimoles (mmol)), racemic 1,2-dimethylpropylamine (10.0 g; 114.7 mmol; purchased from Aldrich) and triethylamine (11.61 g; 114.7 mmol) was heated under reflux for 5 hours. Concentrated sodium hydroxide solution was added to neutralize hydrobromide salts, and the resulting mixture was twice extracted with diethyl ether. Ether layers were combined and dried over anhydrous magnesium sulfate. The drying agent was then removed by filtration, and the solvent was removed by evaporation. The colorless liquid residue was distilled by short-path distillation to yield about 3.5 g (26%) of the desired amine, having a boiling point of 114°–118° C.

b) In-situ preparation of S-benzyl chloroformate

To a solution of triphosgene (5.0 g; 16.85 mmol) in 80 ml of methylene chloride was added dropwise over 45 minutes a solution containing benzyl mercaptan (5.40 g; 43.47 mmol) and triethylamine (4.90 g; 48.4 mmol) in 120 ml methylene chloride. After addition was complete, the reaction mixture was stirred for another 10 minutes at ambient temperature.

c) Preparation of thiocarbamate

To the solution of S-Benzyl chloroformate prepared above was added dropwise over 15 minutes a solution of (±) 1,2 dimethylpropyl(-ethyl)amine, (5.00 g; 43.4 mmol), prepared as in 1(a) above, and triethylamine (4.90 g; 48.4 mmol) in 30 ml of methylene chloride. After addition was complete, stirring was continued for 1 hour at ambient temperature. The reaction solution was washed twice with 250 ml portions of water, the organic phase then dried over anhydrous magnesium sulfate. The magnesium sulfate was removed by filtration and the solvent was removed by evaporation to leave 11.40 g of slightly yellow viscous liquid residue. The liquid residue was chromatrographed on silica gel by first eluting with a large volume of hexanes to remove a less polar impurity., di-(S-benzyl) carbonate and then with a mixture of 95% hexanes 5% ethyl acetate to recover the racemic thiocarbamate as a colorless viscous liquid (6.0 g; 52% yield). The product was 97.3% pure as determined by GC.

Example 2

Preparation of (±)-S-benzyl 1,2-dimethylpropylthiocarbamate

A solution of S-benzylchloroformate was prepared in an according to the method of Example 1(b) above, from a solution of 7.12 g (57.3 mmol) of benzyl mercaptan, 6.47 g (21.8 mmol), triphosgene and 6.4 g (63.25 mmol) triethylamine in 100 ml methylene chloride. To this solution was then added dropwise with stirring a solution containing 5.00 g (57.4 mmol) of (±)-1,2-dimethylpropylamine and 6.40 g (63.25 mmol) of triethylamine in 40 ml of methylene chloride. The resulting reaction solution was stirred at ambient temperature for an additional hour, washed twice with 250 ml portions of water, and then dried over anhydrous magnesium sulfate. After removal of the magnesium sulfate, the solvent was evaporated leaving a white solid product weighing, after prolonged drying under high vacuum, 10.73 g. Product yield was 79%.

Example 3

Preparation of R(−) and S(+) 1,2-dimethylpropylamine

The enantiomers of 1,2-dimethylpropylamine were prepared by biosynthesis, using (R) and (S) transaminases prepared according to the method described in U.S. Pat. No. 4,950,606, (the disclosure of which is hereby incorporated herein in its entirety) with methyl isopropyl ketone (100 mM) as the amine acceptor and isopropylamine (0.5M) as the amine donor. The reactions were performed over a 24 hour period at pH 7.5 in 100 mM phosphate buffer, in the presence of 2 millimoles of pyridoxal phosphate. At the end of the reaction period., the reaction batch was cooled to 4°–10° C. and centrifuged at 5000 g for 10 minutes to remove debris.

The pH was adjusted to about 1.0 with concentrated HCl. The mixture was concentrated about six-fold by distillation to remove ketones and water. The concentrate was chilled in an ice bath while the pH was adjusted to about 12 with concentrated NaOH. The resulting solution was distilled until the vapor temperature reached 100° C. The distillate fraction was dried over magnesium sulfate. After removal of the magnesium sulfate, the mixture was distilled through a distillation column packed with glass helices to effect separation of isopropylamine and the desired product amine that was collected at 80°–87° C. Fractions obtained in this manner typically contained a small amount of residual water that was removed with magnesium sulfate. The specific rotations of the amines at 22° C. were about 3.8° (neat): R(−), S(+); the R(−) enriched amine, prepared in several steps from L-valine and that was 46% racemized, was reported to have a specific rotation of −1.80 (neat); Rubinstein, et al., J. Chem. Soc. Perkin Tran., 16 II, 2094 (1973).

The enantiomeric excess of each of the amines prepared as above, was determined to be >99%, using Marfey's reagent (Nα-(2,4-Dinitro-5-fluorophenyl)-L-alaninamide; available from Aldrich, catalog no. 36,605-6). HPLC analysis of the derivatized amines was performed with a Novapak Phenyl 8 mm×10 mm column eluting with 70% water/30% isopropyl alcohol at a flow rate of 1.8 ml/min. Retention time for the R(−) derivative was about 31.5 minutes, while that of the S(+) isomer derivative was about 33.5 min. The derivatization procedure employed 0.8 ml of Marfey's reagent (0.68 mg/ml in acetone) 0.1 ml of the amine in 10 mM HCl, and 0.16 ml of 0.1M NaHCO$_3$. The mixture was heated at 60° C. for 1 hour and then the reaction was quenched by addition of 0.4 ml of 2N HCl. After dilution with 0.2 ml of water the sample was injected for the analysis.

Example 4

Preparation of R(−) and S(+) 1,2-dimethyl propyl (ethyl)amine

The parent R(−) and S(+) 1,2-dimethylpropylamines were converted to the ethylated secondary amines as in Example 1 (a). From 5.00 g (57.4 mmol) of the R(−) enantiomer 6.0 g (59.5 mmol) triethylamine, and 15.00 g (119.3 mmol) of bromoethane a 266 yield of the desired R(−) 1,2 dimethylpropyl(ethyl)amine was obtained. Using the same procedure, the S(+) 1,3-dimethylpropyl (ethyl)amine was obtained in 28% yield.

Example 5

Preparation of R(−) and S(+) S-benzyl 1,2-dimethylpropyl (ethyl)thiocarbamate

The preparations were performed from the appropriate enantiomer (Prepared according to Example 4), using in-situ generation of S-benzyl chloroformate as in Example 1-b and conversion to the thiocarbamate as in Example 1-c. In this way from 1.5 gm (5.1 mmol) of triphosgene, 1.62 gm (13.0 mmol) of benzyl mercaptan, and 1,50 gm (14.8 mmol) triethylamine in 25 ml of methylene chloride to which was added a solution of 1,50 gm (13.0 mmol) of S(+) 1,2-dimethylpropyl (ethyl)amine and 1.50 gm (14.8 mmol) of triethylamine in 10 ml of methylene chloride, there was obtained 1.7 gm (49%) of the desired S(+) S-benzyl 1,2-dimethylpropyl (ethyl)thiocarbamate: $[\alpha]_D^{22}$=+17.33° (C=25.1, methanol).

In a like manner, R(−) 1,2-dimethylpropyl(ethyl)amine was converted to R(−)S-benzyl 1,2-dimethylpropyl (ethyl) thiocarbamate in 43% yield: $[\alpha]_D^{22}$=−17.50° (C=25.15, methanol).

Example 6

Herbicidal screening, first round

Test materials were applied to 13 plant species at five rates in order to evaluate their herbicide efficacy properties. Five common broadleaf weed species and five common grass species were treated with a pre-emerge and a post-emerge application of the test materials (see list below). For pre-emerge, seeds were planted one day prior to application of the test materials. For post-emerge, plants were treated at the 2–3 leaf stage (2"–4" tall). In addition, three crop species, corn, soybean and upland rice, were treated in order to determine the crop safety potential of the test materials. Test materials were applied at 31, 63, 125, 250 and 500 g active ingredient per acre (ai/acre).

At 2 weeks after application, a visual control rating (0–100) was assigned for each species. With this rating system 0=no control and 100=complete death of all plants in the pot. For weed species, a GR80 was calculated, ie. that rate which causes an 80% reduction in growth. For crop species a GR20 was calculated. With these values, weed control spectrum and crop safety can be determined.

Table 1 lists the species on which the compounds were tested in the first round of screening. Table 2 lists the GR80 and GR20 for the compounds tested on the species in Table 1.

The data in Table 2 indicate that the R(−) enantiomer was more effective against Setaria viridis, Echinochloa crusgalli, and Agropyron repens than the racemate, as the GR80 is lower for the R(−) enantiomer. The difference in activity between the R(−) enantiomer and the S(+) enantiomer is even more marked.

TABLE 1

| Bayer code and common name of species screened | |
|---|---|
| BAYER CODE | BOTANICAL NAME |
| AMARE | *Amaranthus retroflexus* |
| ABUTH | *Abutilon theophrasti* |
| AMBEL | *Ambrosia artemisifolia* |
| IPOHE | *Ipomosa hederacea* |
| CHEAL | *Chenopodium album* |
| SETVI | *Setaria viridis* |
| ECHCG | *Echinochloa crus-galli* |
| SORHA | *Sorghum halepense* |
| DIGSA | *Digitaria sanguinalis* |
| AGRRE | *Agropyron repens* |

TABLE 2

Pre-emergence herbicidal activity on grass species

| Compound | SETVI | ECHCG | SORHA | DIGSA | AGGRE | Mean Across Grasses | RICE | MAIZE |
|---|---|---|---|---|---|---|---|---|
| | GR80 | | | | | | GR20 | |
| R(−) | 234 | 340 | 373 | 397 | 260 | 321 | 477 | NA |
| RS(+/−) | 349 | 381 | 394 | 463 | 297 | 377 | >500 | NA |
| S(+) | 419 | 487 | 330 | 367 | 590 | 439 | >500 | NA |
| RAC/DES | NA | NA | NA | NA | NA | NA | NA | NA |

NA = No activity.
R(−) = R(−)-S-benzyl-1,2-dimethylpropyl(ethyl)thiocarbamate
S(+) = S(+)-S-benzyl-1,2-dimethylpropyl(ethyl)thiocarbamate
RAC/DES = RS(+/−)-S-benzyl-1,2-dimethylpropylthiocarbamate
GR80 = Amount of ai/acre required to provide 80% control of weed species. (Calculated from rate response study.)
GR20 = Amount of ai/acre which causes 20% damage to crop species. (Calculated from rate response study.)

Example 7
Herbicidal activity testing, second round

Three test materials were applied pre-emerge to 7 plant species at 11 rates in order to precisely determine their relative herbicide efficacy. Test materials were applied at 50, 100, 150, 200, 250, 300, 350, 400, 450, 500, and 600 g ai/acre. With these data, advanced statistical analyses such as parallel line analysis were conducted.

At 2 weeks after application, percent control ratings (0–100) were recorded (0=no control and 100=complete death of all plants in the pot). For weed species, a GR80 was calculated, ie. that rate which caused an 80% reduction in growth.

Data are presented in Tables 4 and 5. Table 5 shows pooled data from two repetitions. Table 5 shows mean of two replicates of measurement of herbicidal activity as a function of rate of application.

The data in Table 4 indicate that the R(−) enantiomer is more effective than the racemate and the S(+) enantiomer against *Setaria viridis*, *Echinochloa crus-galli*, *Seteria faberi*, and *Agropyron repens*.

TABLE 3

| Bayer code and botanical name of species screened | |
|---|---|
| BAYER CODE | BOTANICAL NAME |
| CYPES | *Cyperus esculentus* |
| SETFA | *Seteria faberi* |
| SETVI | *Setaria viridis* |
| ECHCG | *Echinochloa crus-galli* |
| SORHA | *Sorghum halepense* |
| DIGSA | *Digitaria sanguinalis* |
| AGRRE | *Agropyron repens* |

TABLE 4

Pre-emergence herbicidal activity on grass species
Pooled Data from two repetitions

| Compound | CYPES | SETVI | ECHCG | SETFA | AGGRE | DIGSA | SORHA | Mean Across Grasses |
|---|---|---|---|---|---|---|---|---|
| | | | | GR80 | | | | |
| R(−) | NA | 346 | 490 | 162 | 418 | 560 | 574 | 425 |
| RS(+/−) | NA | 390 | 709 | 193 | 454 | 438 | 484 | 445 |
| S(+) | NA | 536 | 806 | 261 | 765 | 398 | 703 | 578 |

NA = No activity

GR80 = Amount of ai/acre required to provide 80% control of weed species. (Calculated from rate response study.)

TABLE 5

Pre-emerge herbicidal activity on grass species, as a function of rate of application

| Rate g ai/acre | CYPES | | | SETVI | | | ECHCG | | | SETFA | | | AGGRE | | | DIGSA | | | SORHA | | |
|---|---|---|---|---|---|---|---|---|---|---|---|---|---|---|---|---|---|---|---|---|---|
| | 45 R | 46 S | 47 RS | 45 R | 46 S | 47 RS | 45 R | 46 S | 47 RS | 45 R | 46 S | 47 RS | 45 R | 46 S | 47 RS | 45 R | 46 S | 47 RS | 45 R | 46 S | 47 RS |
| | Percent Control | | | | | | | | | | | | | | | | | | | | |
| 50 | 0 | 0 | 0 | 5 | 0 | 30 | 0 | 0 | 0 | 18 | 5 | 10 | 0 | 0 | 0 | 0 | 0 | 0 | 0 | 0 | 0 |
| 100 | 0 | 0 | 0 | 38 | 0 | 30 | 5 | 0 | 0 | 78 | 35 | 53 | 0 | 0 | 0 | 3 | 0 | 0 | 3 | 0 | 0 |
| 150 | 0 | 0 | 0 | 55 | 0 | 35 | 10 | 0 | 5 | 75 | 73 | 75 | 15 | 0 | 5 | 3 | 25 | 13 | 3 | 13 | 10 |
| 200 | 0 | 5 | 0 | 60 | 18 | 65 | 8 | 0 | 35 | 88 | 85 | 88 | 25 | 0 | 25 | 8 | 28 | 40 | 5 | 15 | 28 |
| 250 | 0 | 5 | 0 | 75 | 40 | 75 | 25 | 10 | 40 | 94 | 80 | 88 | 55 | 13 | 40 | 25 | 45 | 30 | 8 | 18 | 35 |
| 300 | 5 | 5 | 0 | 80 | 48 | 70 | 40 | 18 | 45 | 97 | 88 | 95 | 63 | 30 | 60 | 38 | 73 | 45 | 23 | 28 | 55 |
| 350 | 5 | 0 | 0 | 85 | 53 | 83 | 68 | 13 | 50 | 94 | 90 | 97 | 65 | 28 | 67 | 40 | 85 | 70 | 40 | 40 | 58 |
| 400 | 0 | 0 | 0 | 80 | 63 | 83 | 68 | 28 | 48 | 95 | 90 | 95 | 64 | 35 | 73 | 43 | 85 | 85 | 43 | 58 | 70 |
| 450 | 10 | 15 | 25 | 88 | 65 | 88 | 75 | 38 | 55 | 98 | 93 | 98 | 100 | 35 | 72 | 63 | 90 | 88 | 55 | 73 | 80 |
| 500 | 0 | 40 | 25 | 93 | 85 | 88 | 88 | 70 | 75 | 98 | 94 | 97 | 95 | 50 | 97 | 83 | 91 | 88 | 75 | 70 | 78 |
| 600 | 0 | 45 | 10 | 93 | 80 | 88 | 83 | 63 | 70 | 99 | 99 | 99 | 97 | 80 | 90 | 83 | 94 | 95 | 83 | 75 | 94 |
| Mean | 2 | 10 | 5 | 68 | 41 | 67 | 43 | 22 | 38 | 85 | 76 | 81 | 53 | 25 | 48 | 35 | 56 | 50 | 31 | 35 | 46 |

Data are mean of two replicates. The data show that the R-enantiomer provides a greater degree of growth control than the S-enantiomer against 4 of the 6 species tested. The R-enantiomer provides greater growth control over at least half of the species than does the racemate.

Table 6 presents a summary of the test data and an average GR80 for each enantiomer and the racemate against 6 species. The data indicate that, overall, the R-enantiomer is a more effective growth regulator for grassweeds.

TABLE 6

SUMMARY OF TESTING OF PRE-EMERGENT GRASSWEED
HERBICIDE ACTIVITY OF RACEMATE AND ENANTIOMERS
GR80 Values (g ai/acre)

| | | Enantiomer | Round 1 | Round 2 Rep 1 | Round 2 Rep 2 | Average |
|---|---|---|---|---|---|---|
| *Setaria viridis* | SETVI | (R) | 234 | 374 | 283 | 297 |
| | | (S) | 419 | 680 | 449 | 516 |
| | | (RS) | 349 | 383 | 278 | 337 |
| *Echinochloa crus-galli* | ECHCG | (R) | 340 | 561 | 461 | 454 |
| | | (S) | 487 | 732 | 574 | 598 |
| | | (RS) | 381 | 779 | 328 | 496 |
| *Sorghum halepense* | SORHA | (R) | 373 | 511 | 650 | 511 |
| | | (S) | 330 | 630 | 501 | 487 |
| | | (RS) | 394 | 439 | 572 | 468 |
| *Digitaria sanguinalis* | DIGSA | (R) | 397 | 606 | 554 | 519 |
| | | (S) | 367 | 362 | 468 | 399 |
| | | (RS) | 463 | 404 | 378 | 415 |
| *Agropyron repens* | AGRRE | (R) | 260 | 492 | 243 | 332 |
| | | (S) | 590 | 911 | 279 | 593 |
| | | (RS) | 297 | 548 | 572 | 472 |
| *Seteria faberi* | SETFA | (R) | NA | 179 | 161 | 170 |
| | | (S) | NA | 237 | 233 | 235 |
| | | (RS) | NA | 194 | 192 | 193 |

Overall average GR80
G ai/acre
(R) 381
(S) 519
(RS) 438

The data indicate that the R-enantiomer has a lower overall GR80, meaning that less of this enantiomer will provide the same effectiveness as a larger quantity of the racemate or the S-enantiomer.

Various modifications of the invention, in addition to those described herein, will be apparent to those skilled in the art from the foregoing description. Such modifications are intended to fall within the scope of the appended claims.

What is claimed is:

1. A method for inhibiting growth of a plant, comprising applying to the locus of the plant S-benzyl 1,2-dimethylpropyl(ethyl)thiocarbamate, enriched in the R isomer.

2. The method of claim 1 wherein said plant is in a pre-emergent growth state.

3. The method of claim 1 wherein said plant is an annual weed.

4. The method of claim 1 wherein said plant is a common grass species.

5. The method of claim 1 wherein said plant is *Seteria faberi, Setaria viridis, Echinochloa crus-galli,* or *Agropyron repens.*

6. The method of claim 1 wherein said thiocarbamate is differentially herbicidally active toward at least one crop plant.

7. The method of claim 6 wherein the herbicidal activity of said (R)-S-benzyl 1,2-dimethylpropyl(ethyl) thiocarbamate toward a desirable non-weed plant species is less than about 20 percent.

8. S-benzyl 1,2-dimethylpropyl(ethyl)thiocarbamate, enriched in the R isomer.

9. A method for improving the yield of a crop comprising applying to the locus of the crop an herbicidally effective amount of S-benzyl 1,2-dimethylpropyl(ethyl) thiocarbamate enriched in the R isomer.

10. A method for inhibiting the growth of *Seteria faberi, Setaria viridis, Echinochloa crus-galli*, or *Agropyron repens* comprising applying to the locus of the grass an herbicidally effective amount of S-benzyl 1,2-dimethylpropyl(ethyl) thiocarbamate enriched in the R isomer.

\* \* \* \* \*